United States Patent
Partington

(10) Patent No.: US 10,407,356 B2
(45) Date of Patent: Sep. 10, 2019

(54) PROCESS FOR DEHYDRATION OF OXYGENATES WITH HETEROPOLYACID CATALYSTS HAVING MIXED OXIDE SUPPORTS AND USE OF THE SAME

(71) Applicant: TECHNIP E&C LIMITED, Milton Keynes, Buckinghamshire (GB)

(72) Inventor: Stephen Roy Partington, Hull (GB)

(73) Assignee: TECHNIP E&C LIMITED, Milton Keynes, Buckinghamshire (GB)

(*) Notice: Subject to any disclaimer, the term of this patent is extended or adjusted under 35 U.S.C. 154(b) by 10 days.

(21) Appl. No.: 15/537,819

(22) PCT Filed: Dec. 18, 2015

(86) PCT No.: PCT/EP2015/080476
§ 371 (c)(1),
(2) Date: Jun. 19, 2017

(87) PCT Pub. No.: WO2016/097286
PCT Pub. Date: Jun. 23, 2016

(65) Prior Publication Data
US 2018/0009725 A1    Jan. 11, 2018

(30) Foreign Application Priority Data

Dec. 19, 2014  (EP) ..................... 14199345

(51) Int. Cl.
*C07C 1/24* (2006.01)
(52) U.S. Cl.
CPC ............ *C07C 1/24* (2013.01); *C07C 2521/04* (2013.01); *C07C 2521/06* (2013.01);
(Continued)

(58) Field of Classification Search
None
See application file for complete search history.

(56) References Cited

U.S. PATENT DOCUMENTS

| | | | |
|---|---|---|---|
| 2010/0292520 A1* | 11/2010 | Gracey | B01J 23/30 585/324 |
| 2013/0185992 A1* | 7/2013 | Cortright | C10G 3/45 44/438 |
| 2016/0326448 A1* | 11/2016 | Bauldreay | F02C 9/40 |

FOREIGN PATENT DOCUMENTS

WO    WO 2010/146332 A1    12/2010

OTHER PUBLICATIONS

Dilek Varisli et al: "Silicotungstic Acid Impregnated MCM-41-like Mesoporous Solid Acid Catalysts for Dehydration of Ethanol", Industrial & Engineering Chemistry Research, vol. 47, No. 12, Jun. 1, 2008 (Jun. 1, 2008), pp. 4071-4076, XP055190448, ISSN: 0888-5885, DOI: 10.1021/ie800192t—the whole document.

(Continued)

*Primary Examiner* — Philip Y Louie
(74) *Attorney, Agent, or Firm* — David W. Carstens; J. Andrew Reed; Carstens & Cahoon, LLP

(57) ABSTRACT

The present invention relates to a process for producing ethene by the vapor phase dehydration of ethanol using a supported heteropolyacid catalyst. In particular, the present invention involves the use of a supported heteropolyacid catalyst, wherein the supported heteropolyacid catalyst is: i) a mixed oxide support comprising silica and a transition metal oxide, wherein silica is present in an amount of at least 50 wt. %, based on the weight of the mixed oxide support; or ii) a mixed oxide support comprising zirconia and a different transition metal oxide, wherein zirconia is present in an amount of at least 50 wt. %, based on the weight of the mixed oxide support. When used in a process for the preparation of ethene by vapor phase dehydration, and after attaining steady-state performance of the catalyst, the pro- (Continued)

Figure 1:
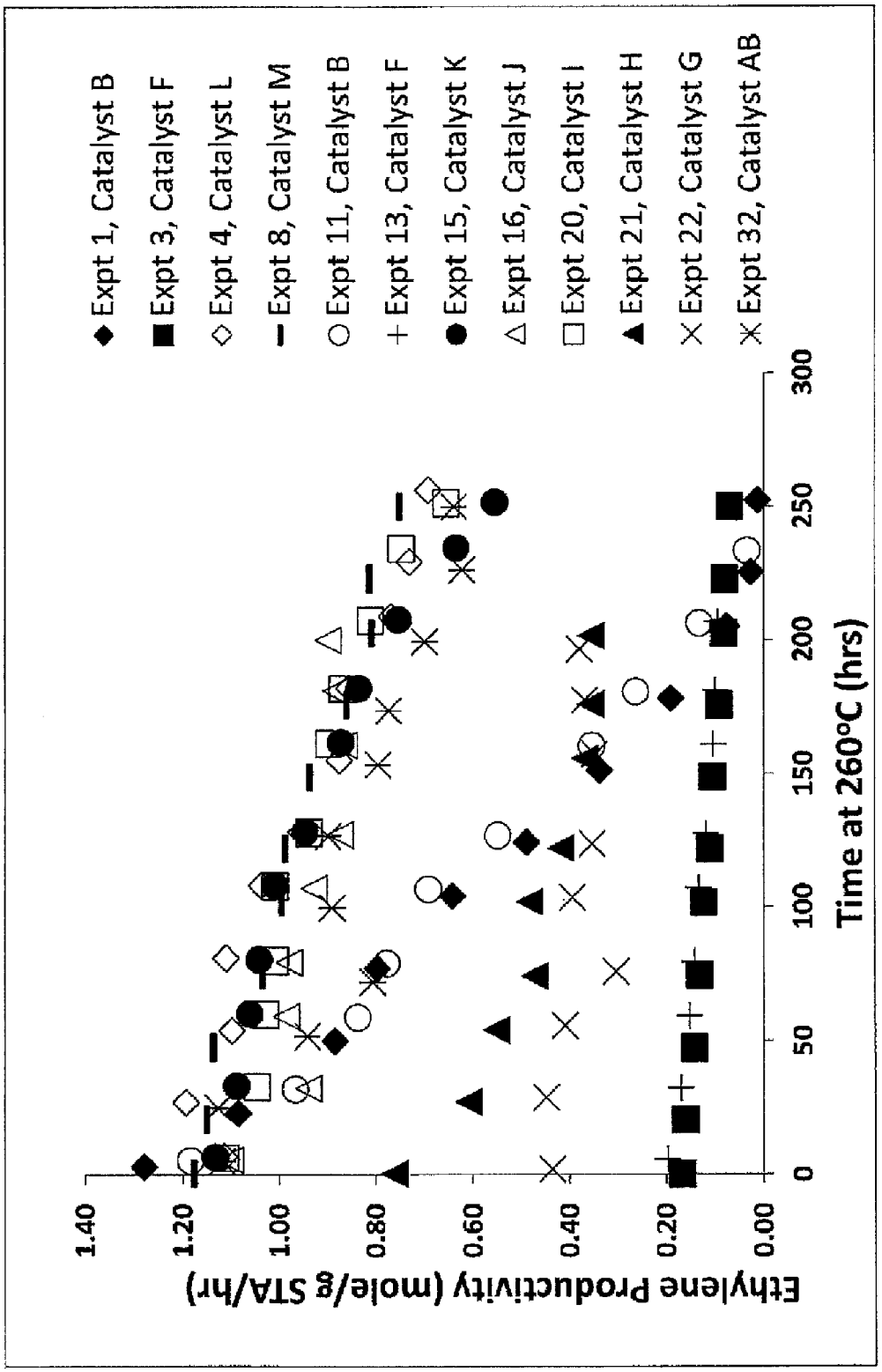

cess may be operated continuously with the same supported heteropolyacid catalyst for at least 150 hours without any regeneration of the catalyst.

16 Claims, 7 Drawing Sheets

(52) U.S. Cl.
CPC ...... *C07C 2521/08* (2013.01); *C07C 2521/12* (2013.01); *C07C 2521/18* (2013.01); *C07C 2523/10* (2013.01); *C07C 2523/20* (2013.01); *C07C 2523/30* (2013.01); *Y02P 20/52* (2015.11); *Y02P 20/584* (2015.11)

(56) References Cited

OTHER PUBLICATIONS

Bachiller-Baeza B et al: "FTIR and Reaction Studies of Styrene and Toluene over Silica-Zirconia-Supported heteropoly Acid Catalysts",Jurnal of Catalysis, Academic Press, Duluth, MN, US, vol. 212, No. 2, Dec. 10, 2002 (Dec. 10, 2002), pges 231-239, XP027233550, ISSN: 0021-9517—the whole document.
International Search Report dated Feb. 23, 2016 for International Application No. PCT/EP2015/080476.

\* cited by examiner

PROCESS FOR DEHYDRATION OF OXYGENATES WITH HETEROPOLYACID CATALYSTS HAVING MIXED OXIDE SUPPORTS AND USE OF THE SAME

CROSS REFERENCE TO RELATED APPLICATIONS

This application is the U.S. national phase of International Application No. PCT/EP2015/080476 filed Dec. 18, 2015, which designated the U.S. and claims priority to European application number 14199345.1 filed Dec. 19, 2014, the entire content of which is hereby incorporated by reference.

The field of the invention is the dehydration of oxygenates to alkenes. More particularly, the present invention relates to a process for producing ethene by the vapour phase dehydration of ethanol using a heteropolyacid catalyst. In particular, the present invention involves the use of a heteropolyacid catalyst having a mixed oxide support, which has been found to exhibit extended catalyst lifetime in an alcohol dehydration reaction compared with conventional supported heteropolyacid catalysts.

Ethene is an important commodity chemical and monomer which has traditionally been produced industrially by the steam or catalytic cracking of hydrocarbons derived from crude oil. However there remains an increasing need to find alternative economically viable methods of making this product. By virtue of its ready availability from the fermentation of biomass and synthesis gas based technologies, ethanol is emerging as an important potential feedstock from which ethene can be made in the future.

The production of ethene by the vapour phase chemical dehydration of ethanol is a well-known chemical reaction which has been operated industrially for many years (see for example Kirk Othmer Encyclopaedia of Chemical Technology (third edition), Volume 9, pages 411 to 413). Traditionally this reaction has been carried out in the presence of an acid catalyst such as activated alumina or supported phosphoric acid.

In recent years attention has turned to finding alternative catalysts having improved performance. This has led to the use of supported heteropolyacid catalysts, such as those disclosed in EP1925363, in the vapour phase chemical dehydration of a feedstock comprising ethanol and ethoxyethane for the production of ethene. Use of such catalysts provides improved selectivity, improved productivity and reduced ethane formation. The latter is particularly desirable because firstly ethane is an undesirable by-product and secondly its separation from ethene on a large scale is both difficult and energy intensive. Related documents WO 2007/063281 and WO 2008/062157 also disclose methods of carrying out dehydration of oxygenate feedstocks with supported heteropolyacid catalysts.

In the ethanol dehydration process, a feed typically comprising ethanol, optionally water and other components (e.g. ethoxyethane) is continuously fed to a reactor containing a bed of heteropolyacid catalyst and the products continuously removed. Under steady-state conditions, the feed entering the reactor is rapidly converted near the inlet into an equilibrium mixture of water, ethanol and ethoxyethane (the product of a rapid first stage dehydration of the ethanol). Such processes are typically conducted at elevated temperature and pressure.

It is known that oxygenate dehydration can lead to carbon build-up on acidic catalysts, such as silicotungstic-$SiO_2$, which leads to catalyst deactivation. Carbon lay-down leading to heteropolyacid catalyst deactivation is, for instance, mentioned in WO 2008/138775. That document teaches that the use of a pure silica support with a particular heteropolyacid loading can give reduced carbon formation on the catalyst in the ethanol dehydration reaction.

U.S. Pat. No. 8,604,234 describes the use of a mixed oxide support for a heteropolyacid catalyst for use in a process for preparing acrolein from glycerol. The mixed oxide support corresponds to a silica modified by zirconia grafting. According to that disclosure, the mixed oxide support is said to confer excellent acrolein selectivity and also provides a catalyst that, once deactivated as a result of carbon deposition, is easily regenerated by means of coke combustion.

Zirconia is known to improve the thermal stability, and chemical resistance to alkaline attack, of a $SiO_2$ based mixed oxide support material. Surface acidic properties of the support are believed to be developed which are normally absent in either of the corresponding single-component oxides. Indeed, these mixed oxide materials have been used as solid acid catalysts in their own right (Journal of Catalysis 212, 231-239). Journal of Catalysis 281, 362-370 also discloses a zirconia modified by niobium used itself as a selective solid acid catalyst for the conversion of glycerol to acrolein. That mixed oxide solid acid is said to also have high stability, which is attributed to the neutralisation of Lewis acid sites on the zirconia which are not selective for reaction with glycerol yet which may otherwise represent coke initiator sites.

There has hitherto been no suggestion in the art that mixed oxides could be used for achieving any specific advantage as supports for heteropolyacid catalysts in a monohydric alcohol dehydration reaction over their single oxide counterparts. WO 2010/146332 describes the use of a supported phosphotungstic acid catalyst in the dehydration of ethanol where the support may be selected from a wide variety of supports, including silica-alumina, silica-titania and silica-zirconia. However, there are no examples of a heteropolyacid catalyst supported with such mixed oxides and there is certainly no suggestion of any advantages of mixed supports over single oxide supports.

The present invention is based on the surprising discovery that a particular mixed oxide support can extend catalyst lifetime in a heteropolyacid catalysed ethanol dehydration reaction by reducing coke deposits that otherwise lead to catalyst deactivation. As such, an ethanol dehydration process can be continuously operated with the same supported heteropolyacid catalyst, without recourse to catalyst regeneration, for longer periods of time than with heteropolyacids supported on single oxide supports. The particular mixed oxide support is either silica or zirconia based (i.e. comprising more than 50 wt. % silica or zirconia) and comprising a transition metal oxide (which transition metal is not zirconium in the case of the zirconia based support). The beneficial effects of the invention are not obtained with single oxide supports, such as pure silica, alumina, zirconia or carbon. Moreover, silica-alumina supports, such as those appearing in the long list of possible supports in WO 2010/146332, also do not give rise to such benefits, and in fact exacerbate catalyst deactivation at high alumina concentrations.

Thus, according to a first aspect, the present invention provides a process for the vapour phase chemical dehydration of ethanol in a reactor in the presence of a supported heteropolyacid catalyst, wherein the support of the supported heteropolyacid catalyst is: i) a mixed oxide support comprising silica and a transition metal oxide, wherein silica is present in an amount of at least 50 wt. %, based on the weight of the mixed oxide support; or ii) a mixed oxide support comprising zirconia and a different transition metal oxide, wherein zirconia is present in an amount of at least 50 wt. %, based on the weight of the mixed oxide support; and wherein, after attaining steady-state performance of the catalyst, said process is operated continuously with the same supported heteropolyacid catalyst for at least 150 hours without any regeneration of the catalyst.

Reference herein to the steady-state performance of the heteropolyacid catalyst is intended to mean the point at which a constant level of activity and selectivity of the catalyst is achieved under the operating conditions of the process, where "constant level" means that there is 5% or less change in activity and selectivity over a period of at least 5 hours of operation. Preferably, there is 2% or less change in activity and selectivity, more preferably 1% or less, even more preferably 0.5% or less, most preferably 0.1% or less, for example 0%, over a period of at least 5 hours of operation. Once steady-state performance of the heteropolyacid catalyst has been attained, it may be desirable to subsequently change operating conditions during a run (for example, pressure and/or temperature) and thereby modify the selectivity and/or activity of the catalyst. However, changes in operating conditions following attainment of steady-state performance do not affect the calculation of the time period for operation with the same catalyst in accordance with the present disclosure. For the avoidance of doubt, the time period referred to herein for operation with the same catalyst without regeneration thereof begins upon the attainment of initial steady-state performance of the catalyst and ends once operation of the dehydration process with the catalyst substantially ceases, for instance in order to conduct catalyst regeneration or shut down the reactor such as for catalyst replacement.

In a preferred embodiment of this first aspect of the present invention, after attaining steady-state performance of the catalyst, the process is operated continuously with the same supported heteropolyacid catalyst for at least 200 hours, more preferably for at least 250 hours, and even more preferably for at least 300 hours, or even longer, such as at least 500, at least 1000, at least 2000 or at least 5000 hours, without any regeneration of the catalyst.

In some embodiments of the present invention, after attaining steady-state performance of the catalyst, the heteropolyacid catalyst retains at least 25%, preferably at least 50%, more preferably at least 75% and even more preferably at least 85% of its maximum activity, observed for the operating temperature under steady-state conditions, after at least 200 hours of operation of the process, preferably at least 250 hours of operation of the process, more preferably at least 300 hours or any other of the operating times in the paragraph above. Any combination of the operating times and activity percentages herein may be made. The catalyst activity is determined as an average across the catalyst bed based on the overall productivity of the bed.

Heteropolyacids supported by a mixed oxide material in accordance with the present invention exhibit significantly extended catalyst lifetime in comparison to alternative or conventional single oxide supported heteropolyacid catalysts. This has clear economic benefits relating to re-use and replacement or regeneration of the catalyst, as well as the reduction of waste. The term "regeneration" used herein refers to the process of re-activating a heteropolyacid catalyst material that has become deactivated (e.g. by coke deposition thereon) by, for instance, coke combustion procedures or the like, or extracting heteropolyacid from a used catalyst for preparing a fresh catalyst.

Without being bound by any particular theory, the mixed oxide support is believed to affect the prevalence and distribution of acid sites of the mixed oxide support and thought to cause changes in the electronic interactions between the heteropolyacid catalyst and the support, modifying the Brønsted acidity of the heteropolyacid catalyst. Consequently, the dominant surface chemistry of the supported heteropolyacid catalyst is modified such that its propensity for deactivation, for instance by carbon lay-down and other deactivation mechanisms, is reduced. For instance, changes in the concentration and/or distribution of active sites on the heteropolyacid is thought to reduce the possibility for unwanted side reactions such as oligomerisation and reactions leading to the formation of coke precursors. These benefits are considered to extend to substantially all heteropolyacid monohydric alcohol dehydrations.

Thus, in a second aspect, the present invention also provides a use of a supported heteropolyacid catalyst comprising a mixed oxide support for increasing catalyst lifetime in a monohydric alcohol dehydration process, preferably in an ethanol dehydration process, wherein the supported heteropolyacid catalyst comprises i) a mixed oxide support comprising silica and a transition metal oxide, wherein silica is present in an amount of at least 50 wt. %, based on the weight of the mixed oxide support; or ii) a mixed oxide support comprising zirconia and a different transition metal oxide, wherein zirconia is present in an amount of at least 50 wt. %, based on the weight of the mixed oxide support.

The oxygenate feedstock in a monohydric alcohol dehydration process in accordance with the second aspect of the invention comprises alcohol(s) optionally together with ether(s). Preferably, the oxygenate feedstock comprises at least one monohydric aliphatic alcohol have one or more alpha hydrogen(s) present, e.g. ethanol, n-propanol and t-butanol. The preferred monohydric aliphatic alcohol(s) are ethanol, propanol, or a mixture thereof, for example, a mixture of ethanol and n-propanol and/or iso-propanol. In preferred embodiments, the oxygenate feedstock comprises a mixture of ethanol and n-propanol for dehydration into the corresponding target alkene(s). The term 'target alkenes' used herein is intended to mean the alkenes that are produced according to the dehydration process of oxygenate feedstock to olefins and preferably consist of either ethene or propene or a mixture thereof.

In particularly preferred embodiments, the monohydric alcohol dehydration process according to the above use of the present invention is an ethanol dehydration process. Thus, in this embodiment, the oxygenate feedstock comprises ethanol.

The dehydration of the feedstock according to the present invention is believed (Chem. Eng Comm. 1990, 95, 27 to 39) to proceed by either the direct dehydration to olefin(s) and water (such as illustrated in relation to the dehydration of ethanol in Equation 1); or via an ether intermediate (such as illustrated in relation to the etherification of ethanol and dehydration of ethoxyethane in Equations 2 and 3).

  (1)

  (2)

  (3)

The direct conversion of the ether to two moles of olefin and water has also been reported (Chem. Eng. Res. and Design 1984, 62, 81 to 91). All of the reactions shown above are typically catalysed by Lewis and/or Brønsted acids. Equation 1 shows the endothermic direct elimination of ethanol to ethene and water; competing with Equation 1 are Equations 2 and 3 i.e. the exothermic etherification reaction (Equation 2), and the endothermic elimination of ethoxyethane to produce ethene and ethanol (Equation 3). However, the dehydration reaction of ethanol to ethene is overall said to be endothermic.

In aspects and embodiments of the present invention, there is provided a process or use comprising the preparation of ethene by vapour phase chemical dehydration of ethanol, said dehydration reaction comprising contacting a feed-stream comprising ethanol in a reactor with a supported heteropolyacid catalyst, wherein the support comprises a mixed oxide as defined hereinbefore. Preferably, the feed-stream comprising ethanol further comprises water and/or ethoxyethane, more preferably water and ethoxyethane.

Suitably, in the aspects and embodiments of the present invention which relate to the vapour phase chemical dehydration of ethanol, the amount of water in the feed-stream is at most 50 wt %, more preferably at most 20 wt %, most preferably at most 10 wt %, or even at most 7 wt %, based on the total weight of water, ethanol and ethoxyethane in the reactant feed-stream. Preferably, the amount of water in the feed-stream is at least 0.1 wt %, more preferably at least 0.5 wt % and most preferably at least 1 wt %, based on the total weight of water, ethanol and ethoxyethane in the feed-stream.

Suitably, in the aspects and embodiments of the present invention which relate to the vapour phase chemical dehydration of ethanol, the amount of ethoxyethane in the feed-stream is at most 50 wt. %, more preferably at most 40 wt. %, most preferably at most 35 wt. %, based on the total weight of water, ethanol and ethoxyethane in the feed-stream. Preferably, the amount of ethoxyethane in the feed-stream is at least 0.1 wt. %, more preferably at least 0.5 wt. % and most preferably at least 1 wt. %, based on the total weight of water, ethanol and ethoxyethane in the feed-stream.

The liquid product stream following olefin removal comprises mostly unreacted alcohols, ethers and water. In the aspects and embodiments of the present invention which relate to the vapour phase chemical dehydration of ethanol, the liquid product stream following ethene removal comprises mostly unreacted ethanol, ethoxyethane and water. The applicants have found that it is particularly preferable to recycle the major portion of the alcohols and ethers back to the vapour phase dehydration reactor after water removal.

In some embodiments of the invention, the feed-stream comprises an inert diluent. In other embodiments, an inert diluent is added down the catalyst bed, or between multiple catalyst beds arranged in series or in parallel, if used. Preferred diluents comprise nitrogen, helium, ethene and/or saturated hydrocarbons, for example hexanes, 2-methylpropane or n-butane. More preferably, the feed-stream diluent is selected from nitrogen and/or helium.

The operating conditions under which the dehydration process is conducted are typically such that the dehydration process is always operated in a vapour phase state. In a preferred embodiment, the operating pressure of the dehydration process is always at least 0.1 MPa, preferably 0.2 MPa, below the dew point pressure and/or the dehydration process operating temperature is at least 10° C. above the dew point temperature of the feed-stream entering the vapour phase dehydration reactor and the reaction mixture that is present inside the vapour phase dehydration reactor. The latter is dependent on factors such as the initial feed-stream composition and the degree of conversion within the reactor.

For the purposes of the present invention, the 'dew point temperature' is defined as being a threshold temperature. For example, for a given mixture, at a given pressure, if the system temperature is raised to above the dew point temperature, the mixture will exist as a dry gas. Likewise below the dew point temperature, the mixture will exist as a vapour containing some liquid. And similarly the 'dew point pressure', is defined as being a threshold pressure. For example, for a given mixture, at a given temperature, if the system pressure is below the dew point pressure, the mixture will exist as a dry gas; above the dew point pressure, the mixture will exist as a vapour containing some liquid.

Thus, in some embodiments of the present invention, the feed temperature of the feed-stream comprising ethanol is preferably from 180° C. to 270° C., more preferably from 190° C. to 260° C. and most preferably from 200° C. to 260° C. Reference to "feed temperature" herein is intended to refer to the temperature of a particular stream at the point at which it is fed to the reactor. The vapour phase reactor used for dehydrating the oxygenates is preferably operated at an internal pressure of from 0.1 MPa to 4.5 MPa, more preferably at a pressure of from 1.0 MPa to 3.5 MPa, still more preferably at a pressure of from 2.0 MPa to 3.5 MPa, and most preferably at a pressure of from 2.5 MPa to 3.3 MPa.

Reference herein to the pressure inside the reactor corresponds to the sum of the partial pressures of the reactants as well as the partial pressure of the product, for instance, in the aspects and embodiments of the present invention which relate to the vapour phase chemical dehydration of ethanol, those of ethanol, water, ethoxyethane, and ethene. Unless otherwise indicated herein, partial pressures of inert gas diluents, such as helium and nitrogen, or other inert components are excluded from the total stated pressure. Thus, in the aspects and embodiments of the present invention which relate to the vapour phase chemical dehydration of ethanol, reference to reactor pressure herein is in accordance with the formula: $P_{reactor}=P_{water}+P_{ethanol}+P_{ethoxyethane}+P_{ethene}$. Furthermore, unless otherwise indicated, reference to reactor pressures herein is to absolute pressures, and not gauge pressures.

In some aspects and embodiments of the present invention which relate to the vapour phase chemical dehydration of ethanol, the feed temperature of the feed-stream comprising ethanol is preferably from 180° C. to 270° C., more preferably from 190° C. to 260° C. and most preferably from 200° C. to 260° C. Reference to "feed temperature" herein is intended to refer to the temperature of a particular stream at the point at which it is fed to the reactor. The vapour phase reactor used for the dehydration reaction is preferably operated at an internal pressure of from 0.1 MPa to 4.5 MPa, more preferably at a pressure of from 1.0 MPa to 3.5 MPa, still more preferably at a pressure of from 2.0 MPa to 3.5 MPa, and most preferably at a pressure of from 2.5 MPa to 3.3 MPa.

In other in the aspects and embodiments of the present invention which relate to the vapour phase chemical dehydration of ethanol, the feed temperature of the feed-stream comprising ethanol is preferably at least 220° C., more preferably at least 240° C. In particular preferred embodiments, the feed temperature is at least 252° C., at least 255° C., at least 260° C., at least 280° C. or even at least 300° C. The upper limit of the feed temperature is below the temperature at which selectivity for ethene is negatively impacted and/or one which is overly energy intensive. Preferably, the upper limit of the feed temperature of the feed-stream is 350° C., more preferably 325° C. In these embodiments, the reactor preferably has an internal pressure of from 0.90 MPa to 1.60 MPa, more preferably from 0.95 MPa to 1.30 MPa, and most preferably from 1.00 MPa to 1.20 MPa.

In accordance with the present invention, the heteropolyacid is supported by a mixed oxide support wherein the support is i) a mixed oxide support comprising silica and a transition metal oxide, wherein silica is present in an amount of at least 50 wt. %, based on the weight of the mixed oxide support; or a mixed oxide support comprising zirconia and a different transition metal oxide, wherein zirconia is present in an amount of at least 50 wt. %, based on the weight of the mixed oxide support.

The mixed oxide support material for use in the present invention may be prepared by any suitable method of which the skilled person is aware, including, for instance, impregnation, grafting, co-precipitation and hydrothermal synthesis techniques. The benefits of the invention have been found not to be dependent upon the specific method by which the mixed oxide is prepared, or by the nature of the distribution of each oxide within the support. This is thought to be as a result of the properties of solid heteropolyacids which may adopt pseudoliquid phases under the operating conditions of the process with discrete and mobile ionic structures, as well as high proton mobility. This is believed to allow for electronic interactions with the support, which may be modified with the presence of a transition metal oxide, regardless of the method by which it is introduced. Thus, for instance, the transition metal oxide may be homogeneously distributed in or through a solid silica or zirconia support structure; may be present as a layer on a previously formed silica or zirconia solid support; or may be enriched in the outer region (i.e. the shell) of the silica or zirconia support particulate.

Suitable mixed oxide catalyst supports may be in a powder form or alternatively may be in a granular form, or in a pelletised form, a spherical form or as extrudates (including shaped particles). As is well known in the prior art, a screw extruder, press extruder, or other extrudation devices may suitably be used for forming extrudates.

The mixed oxide supports used in accordance with the present invention comprise at least one transition metal oxide. Examples of transition metal oxides include oxides of Sc, Y, La, Ti, Zr, Hf, V, Nb, Ta, Cr, Mo, W, Mn, Re, Fe, Ru, Co, Rh, Ni, Pd, Pt, Cu, and Zn. Preferably, the transition metal oxides are selected from Group 3 to 6 metal oxides, more specifically oxides of Sc, Y, La, Ti, Zr, Hf, Nb, Ta and W. More preferably, the transition metal oxides are selected from titania (e.g. $TiO_2$), zirconia (e.g. $ZrO_2$), niobia (e.g. $Nb_2O_5$), yttria (e.g. $Y_2O_3$), lanthana (e.g. $La_2O_3$), and tungsten oxides (e.g. $WO_3$). Most preferably, the transition metal oxides are selected from titania (e.g. $TiO_2$), zirconia (e.g. $ZrO_2$), niobia (e.g. $Nb_2O_5$).

The transition metal oxide is present in the mixed oxide support used in accordance with the invention comprises in an amount of up to 50 wt. %. In one particular embodiment of the process and use of the present invention, the transition metal oxide is present in the mixed oxide support in an amount from 1 to 40 wt. %, preferably from 2 to 35 wt. %.

In preferred embodiments, the mixed oxide support used in accordance with the invention are those mixed oxide supports comprising at least 50 wt. % silica. When used it is more preferred that silica make up at least 60 wt. % silica of the support. Silica based mixed oxide supports include silica in the form of silica gel and supports produced by the flame hydrolysis of $SiCl_4$.

In particularly preferred embodiments, the mixed oxide comprising at least 50 wt. % silica comprises a transition metal oxide selected from an oxide of Nb, Ti, Zr or W, such as titania (e.g. $TiO_2$), zirconia (e.g. $ZrO_2$), niobia (e.g. $Nb_2O_5$), or a tungsten oxide (e.g. $WO_3$); more preferably selected from an oxide of Nb, Ti, or Zr, such as titania (e.g. $TiO_2$), zirconia (e.g. $ZrO_2$) or niobia (e.g. $Nb_2O_5$); most preferably an oxide of Ti or Zr, such as titania (e.g. $TiO_2$) or zirconia (e.g. $ZrO_2$). Thus, for example, the support may comprise silica-titania cogels, silica-zirconia cogels, or silica-niobia cogels.

Suitable silica supports which can be subsequently modified for conversion to a mixed oxide support for use with the present invention include, but are not limited to any of the following: Grace Davison Davicat® Grade 57, Grace Davison Davicat® 1252, Grace Davison Davicat® SI 1254, Fuji Silysia CariAct® Q15, Fuji Silysia CariAct® Q10, Degussa Aerolyst® 3045 and Degussa Aerolyst® 3043. The average diameter of the support particles is about 2 to about 10 mm, preferably about 3 to about 6 mm. However, these particles may be crushed and sieved to smaller sizes of, for example, about 0.5 mm to about 2 mm, if desired. Mesoporous silicas such as commercially available SBA-15, SBA-16, MCM-41 or KIT-6 may also be used following modification by transition metal oxide. The above silica supports may be suitably modified with a transition metal oxide by, for instance, impregnation, adsorption, incipient wetness, or ion-exchange precipitation.

In other embodiments, the mixed oxide support used in accordance with the invention are those mixed oxide supports comprising at least 50 wt. % zirconia. When used it is preferred that the zirconia make up at least 60 wt. % of the support. Zirconia can be prepared, for example, by precipitation of zirconyl nitrate or zirconyl chloride with ammonia at high pH followed by heating under reflux (Calafat., Stud. Surf. Sci. Catal. 118 (1998) 837-843). Alternatively, fine zirconium dioxide powder material can be obtained from zirconyl nitrate and carbohydrazide (Arul Dhas N and Patil K C 1994 Int. J. Self-Propag. High-Temp. Synth. 3, 311). Metastable tetragonal phase zirconia is known to exhibit high strength and high fracture toughness and therefore zirconia based supports comprising that crystalline phase are preferably used in conjunction with the present invention. Powder x-ray diffraction (XRD) techniques can be used for determining crystalline structure ("Introduction to X-ray Powder Diffraction," R. Jenkins and R. L Snyder, Chemical Analysis, Vol. 138, John Wiley & Sons, New York, 1996).

When the mixed oxide support comprises at least 50 wt. % zirconia, it is preferred that the different transition metal oxide which is additionally present is selected from an oxide of W, Ti, Nb, Y or La, such as titania (e.g. $TiO_2$), niobia (e.g. $Nb_2O_5$), yttria (e.g. $Y_2O_3$), lanthana (e.g. $La_2O_3$), and tungsten oxides (e.g. $WO_3$); more preferably an oxide of W, Nb or Ti, such as titania (e.g. $TiO_2$), niobia (e.g. $Nb_2O_5$), and tungsten oxides (e.g. $WO_3$); and even more preferably an oxide of Nb or Ti, such as titania (e.g. $TiO_2$), and niobia (e.g. $Nb_2O_5$). A typical tungsten precursor that may suitably used for preparing tungsten oxide containing support is ammonium metatungstate, which has high solubility and a relatively low price.

Preferred mixed oxide supports are substantially free of extraneous metals or elements which might adversely affect the catalytic activity of the system. It has been found that the presence of alumina has a deleterious effect on the benefits of the invention when present, especially in quantities above 5 wt. % based on the weight of the mixed oxide support. Consequently, it is preferred that the mixed oxide supports used in the present invention comprise less than 5 wt. % of alumina. More preferably, the mixed oxide supports comprises less than 1 wt. % of alumina. Most preferably, the mixed oxide supports comprise substantially no alumina (for example less than 50 ppm, preferably less than 25 ppm, more preferably less than 10 ppm and even more preferably no alumina).

The porosity of the mixed oxide support is not critical for achieving the benefits of the invention and, for instance, mesoporous or microporous supports may both be suitably used with the present invention. Preferably, the average pore radius (prior to impregnation with the heteropolyacid) of the support is about 10 to about 500 Å, preferably about 50 to about 300 Å, more preferably about 60 to about 250 Å and most preferably about 60 to about 250 Å. The pore volume of the support is preferably more than 0.50 ml/g and preferably more than 0.8 ml/g. The BET surface area is preferably from about 50 to about 600 m$^2$/g and is most preferably from about 130 to about 400 m$^2$/g.

The term "heteropolyacid", as used herein and throughout the description of the present invention, is deemed to include inter alia; alkali, alkali earth, ammonium, free acids, bulky cation salts, and/or metal salts (where the salts may be either full or partial salts) of heteropolyacids. Hence, the heteropolyacids used in the present invention are complex, high molecular weight anions comprising oxygen-linked polyvalent metal atoms. Typically, each anion comprises 12-18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:
18-tungstophosphoric acid—$H_6[P_2W_{18}O_{62}].xH_2O$
12-tungstophosphoric acid—$H_3[PW_{12}O_{40}].xH_2O$
12-tungstosilicic acid—$H_4[SiW_{12}O_{40}].xH_2O$
Cesium hydrogen tungstosilicate—$Cs_3H[SiW_{12}O_{40}].xH_2O$
Phosphomolybdic acid—$H_3[PMo_{12}O_{40}].xH_2O$
Silicomolybdic acid—$H_4[SiMo_{12}O_{40}].xH_2O$
Diphosphomolybdic acid—$H_6[P_2Mo_{18}O_{62}].xH_2O$
and the free acid or partial salts of the following heteropolyacids acids:
Monopotassium tungstophosphate—$KH_5[P_2W_{18}O_{62}].xH_2O$
Monosodium 12-tungstosilicic acid—$NaK_3[SiW_{12}O_{40}].xH_2O$
Potassium tungstophosphate—$K_6[P_2W_{18}O_{62}].xH_2O$
Ammonium molybdodiphosphate—$(NH_4)_6[P2Mo_{18}O_{62}].xH_2O$
Potassium molybdodivanado phosphate—$K_5[PMoV_2O_{40}].xH_2O$ In addition, mixtures of different heteropolyacids and salts can be employed. The preferred heteropolyacids for use in the process described by the present invention is any one or more heteropolyacid that is based on the Keggin or Wells-Dawson structures; more preferably the chosen heteropolyacid for use in the process described by the present invention is any one or more of the following: heteropolytungstic acid (such as silicotungstic acid and phosphotungstic acid), silicomolybdic acid and phosphomolybdic acid. More preferably, heteropolyacid for use in the process described by the present invention is silicotungstic acid, for example 12-tungstosilicic acid ($H_4[SiW_{12}O_{40}].xH_2O$), or phosphotungstic acid, for example 12-tungstophosphoric acid ($H_3[PW_{12}O_{40}].xH_2O$). Most preferably, the chosen heteropolyacid for use in the process described by the present invention is silicotungstic acid, for example 12-tungstosilicic acid ($H_4[SiW_{12}O_{40}].xH_2O$).

Preferably, the heteropolyacids employed according to the present invention may have molecular weights of more than 700 and less than 8500, preferably more than 2800 and less than 6000. Such heteropolyacids also include dimeric complexes.

The supported heteropolyacid catalyst may be conveniently prepared by dissolving the chosen heteropolyacid in a suitable solvent, where suitable solvents include polar solvents such as water, ethers, alcohols, carboxylic acids, ketones and aldehydes; distilled water and/or ethanol being the most preferable solvents. The resulting acidic solution has a heteropolyacid concentration that is preferably comprised between 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support), is the preferred method for the purposes of the present invention.

The resulting supported heteropolyacid may be modified, and various salts of heteropolyacid may then be formed in the aqueous solution either prior to, or during, impregnation of the acidic solution onto the support, by subjecting the supported heteropolyacid to a prolonged contact with a solution of a suitable metallic salt or by addition of phosphoric acid and/or other mineral acids.

When using a soluble metallic salt to modify the support, the salt is taken in the desired concentration, with the heteropolyacid solution. The support is then left to soak in the said acidic solution for a suitable duration (e.g. a few hours), optionally with periodic agitation or circulation, after which time it is filtered, using suitable means, in order to remove any excess acid.

When the salt is insoluble it is preferred to impregnate the catalyst with the HPA and then titrate with the salt precursor. This method can improve the dispersion of the HPA salt. Other techniques such as vacuum impregnation may also be employed.

The amount of heteropolyacid impregnated on the resulting support is suitably in the range of 10 wt % to 80 wt % and preferably 20 wt % to 50 wt % based on the total weight of the heteropolyacid and the support. The weight of the catalyst on drying and the weight of the support used, may be used to obtain the weight of the acid on the support by deducting the latter from the former, giving the catalyst loading as 'g heteropolyacid/kg catalyst'. The catalyst loading in 'g heteropolyacid/liter support' can also be calculated by using the known or measured bulk density of the support. The preferred catalytic loading of heteropolyacid is 150 to 600 g heteropolyacid/kg Catalyst.

According to a preferred embodiment of the present invention the average heteropolyacid loading per surface area of the dried supported heteropolyacid catalyst is more than 0.1 micro moles/m$^2$.

It should be noted that the polyvalent oxidation states and hydration states of the heteropolyacids stated previously and as represented in the typical formulae of some specific compounds only apply to the fresh acid before it is impregnated onto the support, and especially before it is subjected to the dehydration process conditions. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is to be expected that such hydration and oxidation states may also be different in the spent catalysts after reaction.

According to a preferred embodiment of the present invention, the amount of chloride present in/on the said heteropolyacid supported catalyst is less than 40 ppm, preferably less than 25 ppm and most preferably less than 20 ppm.

The supported heteropolyacid catalyst used in the process of the present invention may be a fresh catalyst or a previously used catalyst. Thus, in one embodiment, at least a portion of the supported heteropolyacid catalyst has previously been employed in a monohydric alcohol dehydration process, for example in a process for the preparation of an ethene from a feed comprising ethanol and optionally water and ethoxyethane. For example, at least a portion of the supported heteropolyacid may derive from an extract of heteropolyacid from a previously used catalyst i.e. from a partially deactivated material.

According to a further preferred embodiment of the present invention, the heteropolyacid supported catalyst is a heteropolytungstic acid supported catalyst having the following characteristic:

PV>0.6−0.3×[HPA loading/Surface Area of Catalyst]

wherein PV is the pore volume of the dried supported heteropolytungstic acid catalyst (measured in ml/g catalyst); HPA loading is the amount of heteropolyacid present in the dried supported heteropolyacid catalyst (measured in micro moles per gram of catalyst) and Surface Area of Catalyst is the surface area of the dried supported heteropolytungstic acid catalyst (measured in $m^2$ per gram of catalyst).

The BET surface area, pore volume, pore size distribution and average pore radius may be determined from the nitrogen adsorption isotherm determined at 77K using a Micromeritics TRISTAR 3000 static volumetric adsorption analyser. A procedure that may be used is an application of British Standard methods BS4359:Part 1:1984 'Recommendations for gas adsorption (BET) methods' and BS7591:Part 2:1992, Porosity and pore size distribution of materials'—Method of evaluation by gas adsorption. Resulting data may be reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am Chem. Soc., 1951 73 373-380. Samples of supports and catalysts may suitably be gassed for 16 hours at 120° C. under a vacuum of $5\times10^{-3}$ Torr prior to analysis.

In a further aspect, the present invention relates to a composition comprising the product obtained by any of the processes of this invention, or a derivative thereof. As this product arises from the processes of this invention, any features of the processes herein may apply, individually or in any combination, also to this aspect.

Figure 2:
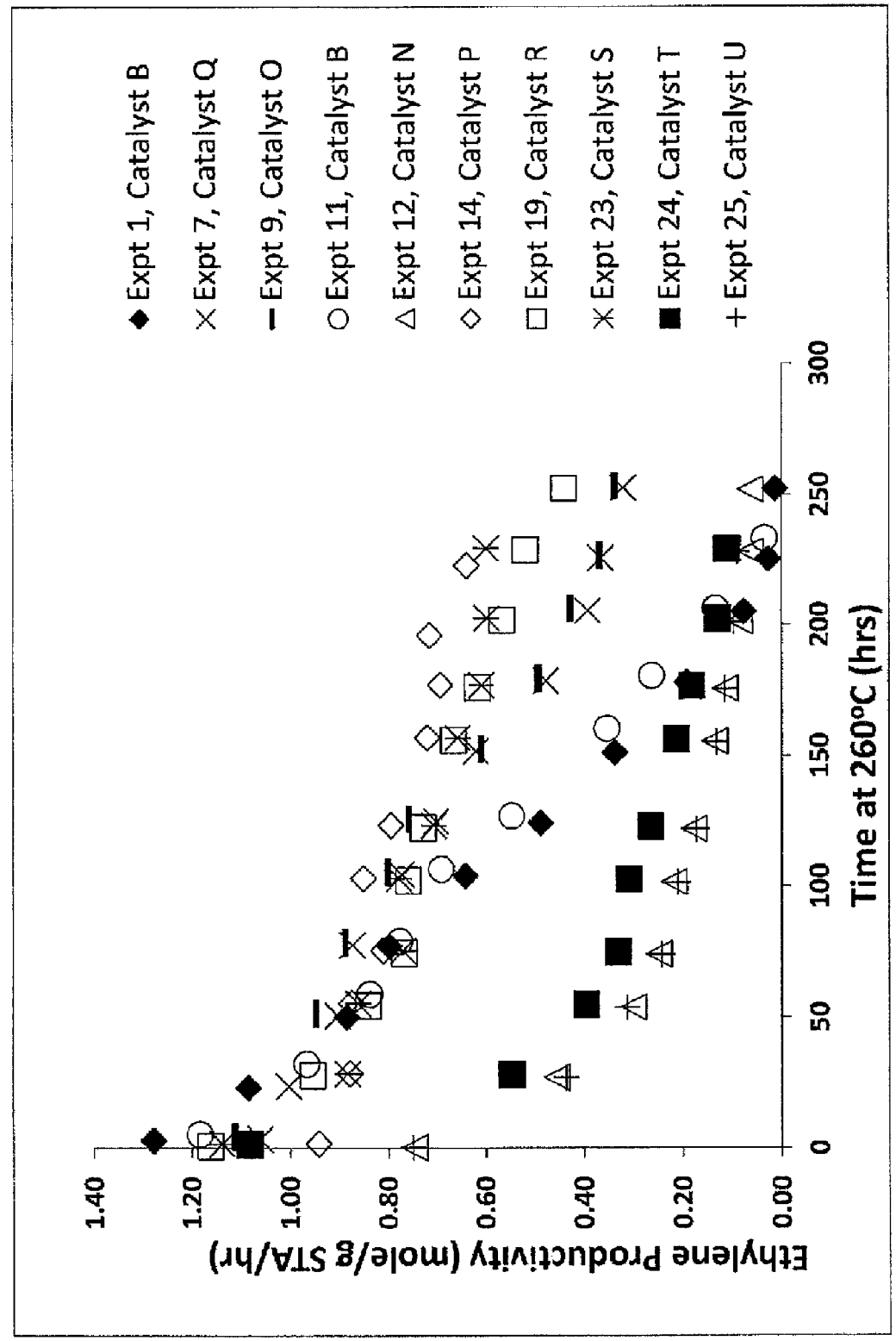
Figure 3:
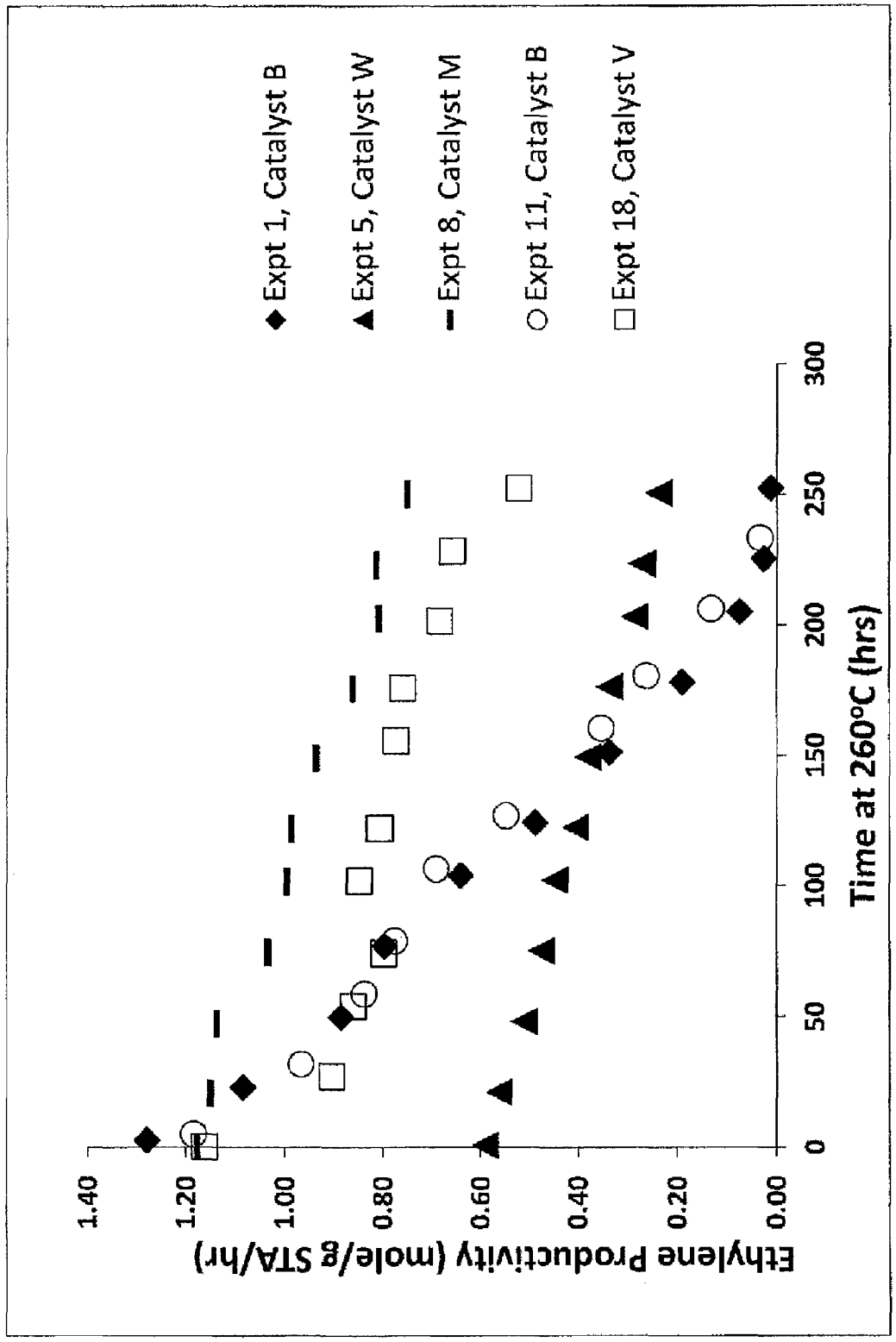
Figure 4:
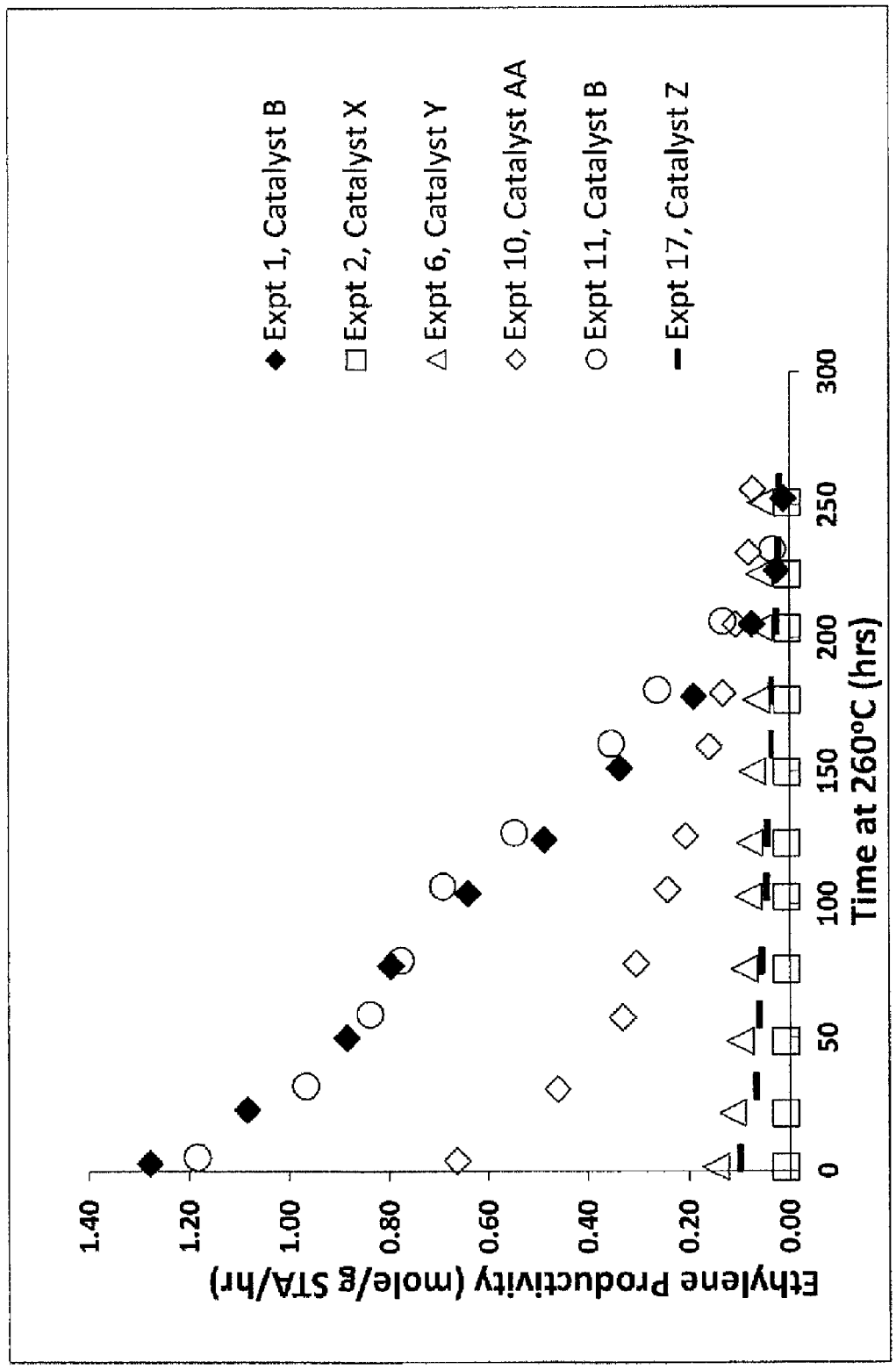
Figure 5:
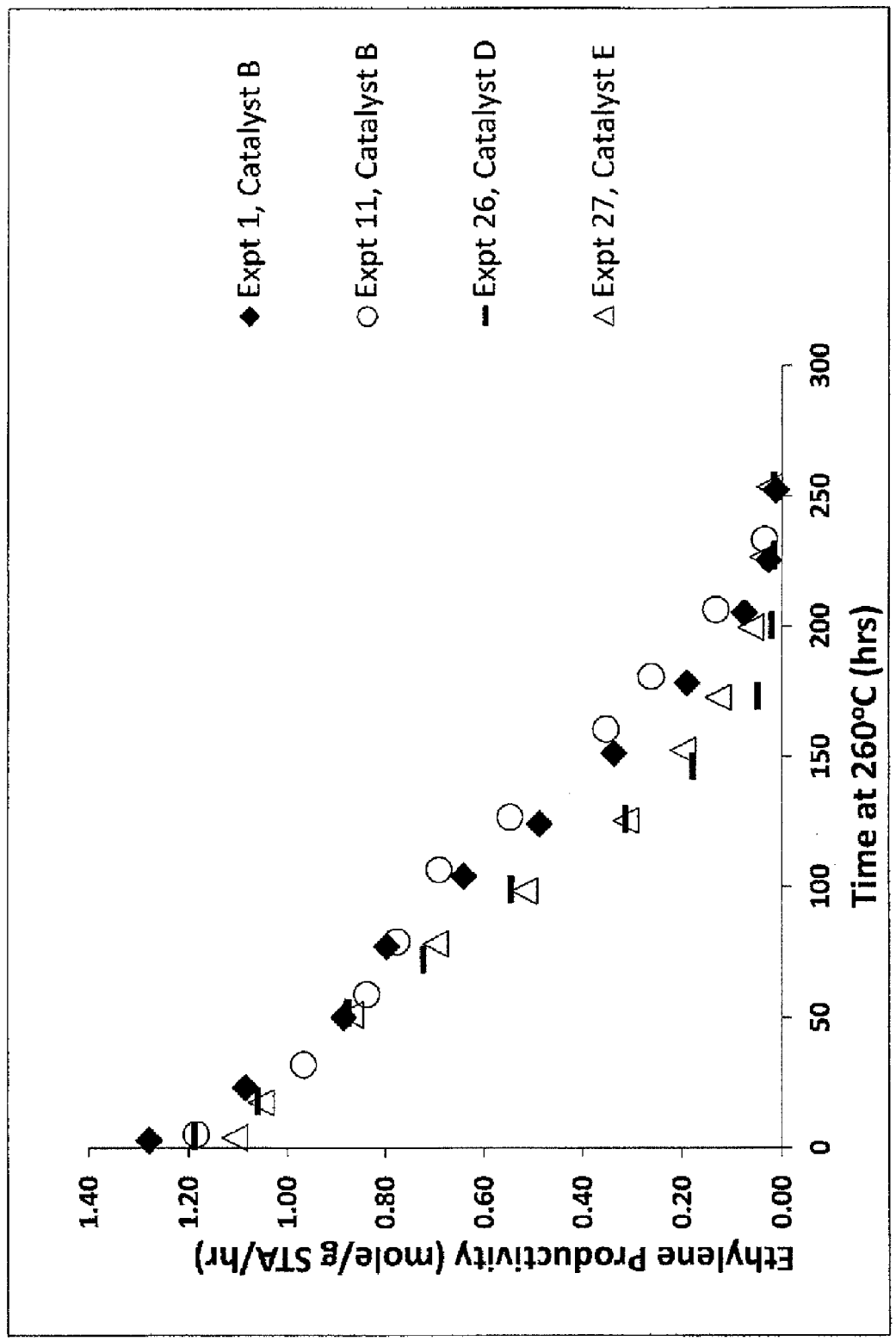
Figure 6:
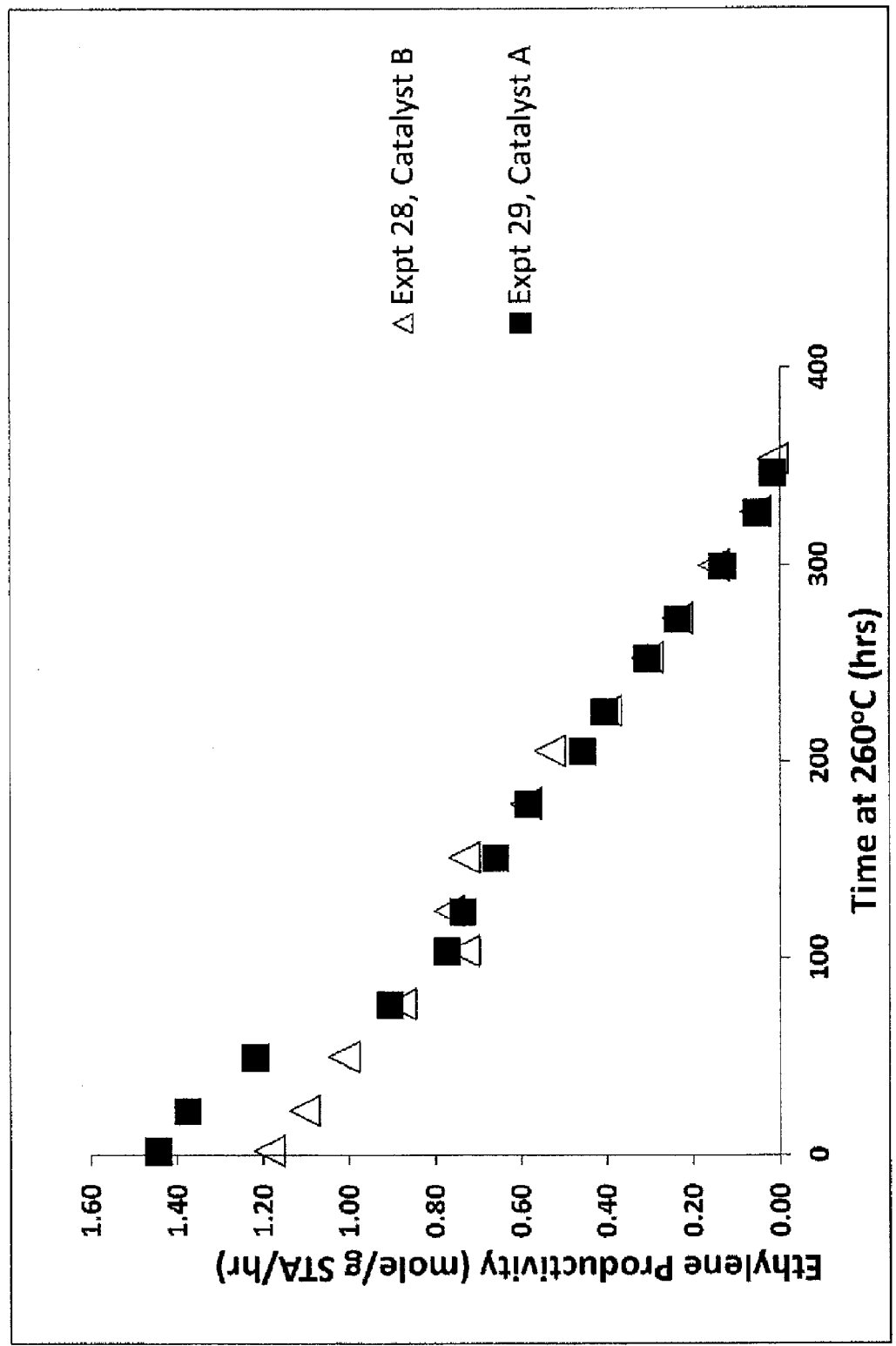
Figure 7:
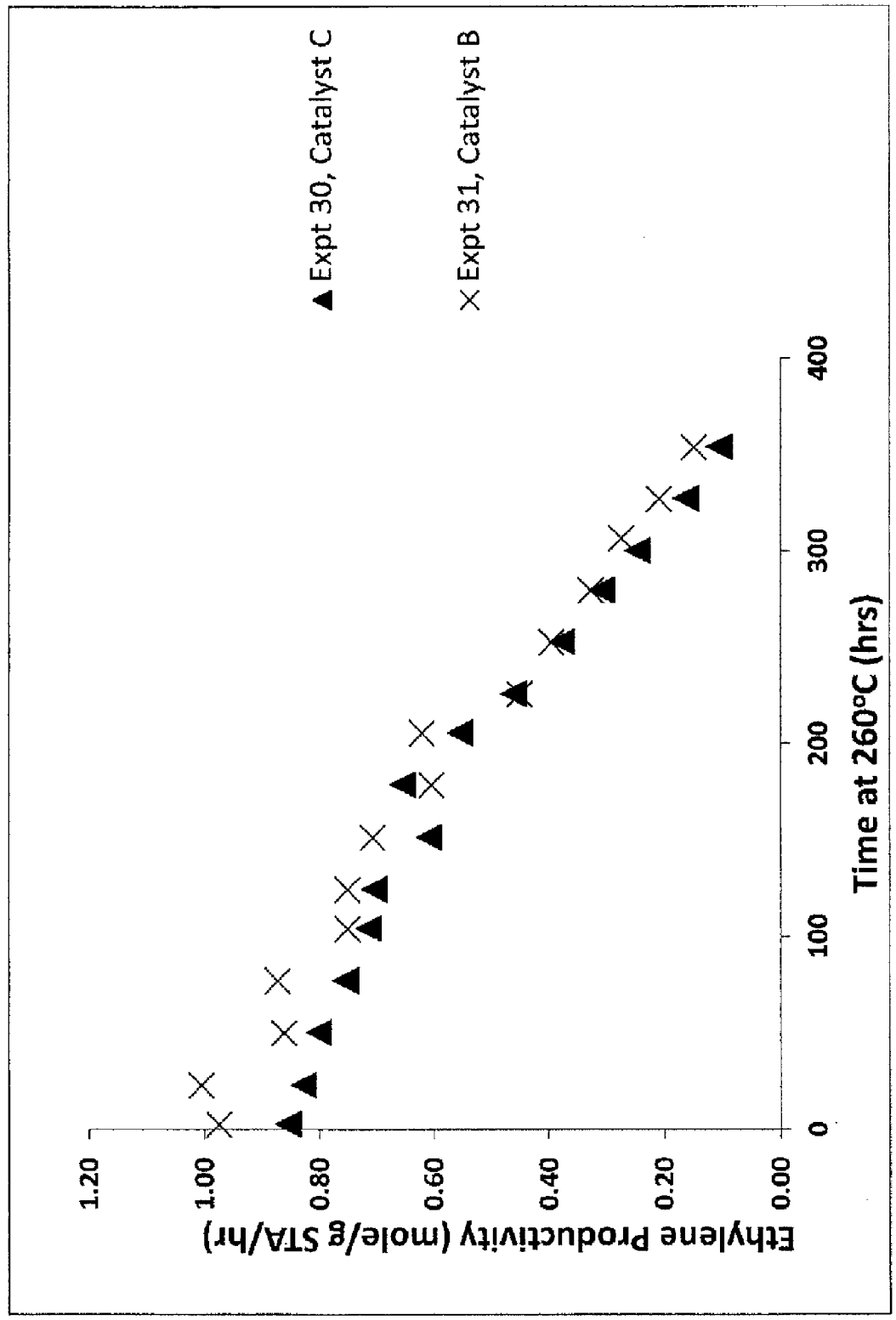

The present invention will now be illustrated by way of the following examples and with reference to the following figures:

FIG. 1: A comparison of results of the vapour phase dehydration of ethanol using catalysts B, F, G, H, I J, K, L, M and AB (Experiments Nos. 1, 3, 4, 8, 11, 13, 15, 16, 20, 21, 22, 32 from Table 3);

FIG. 2: A comparison of results of the vapour phase dehydration of ethanol using catalysts B, N, O, P, Q, R, S, T, U (Experiments Nos. 1, 7, 9, 11, 12, 14, 19, 23, 24 and 25 from Table 3);

FIG. 3: A comparison of results of the vapour phase dehydration of ethanol using catalysts B, M, V and W (Experiments Nos. 1, 5, 8, 11 and 18 from Table 3);

FIG. 4: A comparison of results of the vapour phase dehydration of ethanol using catalysts B, X, Y, Z and AA (Experiments Nos. 1, 2, 6, 10, 11 and 17 from Table 3);

FIG. 5: A comparison of results of the vapour phase dehydration of ethanol using catalysts B, D and E (Experiments Nos. 1, 11, 26 and 27 from Table 3);

FIG. 6: A comparison of results of the vapour phase dehydration of ethanol using catalysts A and B (Experiments Nos. 28 and 29 from Table 3); and FIG. 7: A comparison of results of the vapour phase dehydration of ethanol using catalysts B and C (Experiments Nos. 30 and 31 from Table 3).

EXAMPLES

Preparation of Supported Heteropolyacid Catalyst (Supported Silicotungstic Acid Catalyst)

Table 1 below lists the supports that were used for the preparation of the supported silicotungstic acid catalysts used in the Examples.

TABLE 1

| Support Description/Type |
| --- |
| Silica - Grace Davison G57 |
| Silica - Aerolyst 3045 |
| Silica - Cariact Q15 |
| Alumino-silicate |
| Silica doped with Alumina (7%) |
| Silica-Alumina (25%) |
| γ-Alumina |
| Silica with Niobia (10%) |
| Silica-Titania Cogel (3% $TiO_2$, enriched in shell of $SiO_2$) |
| Silica-Titania Cogel (3% $TiO_2$, dispersed homogeneously throughout $SiO_2$) |
| Silica doped with Titania (5%) |
| Silica-Titania (32%) |
| Silica-Titania (51%) |
| Silica-Titania (70%) |
| Titania (100% with 75% anatase phase) |
| m/t-Zirconia-Titania (41% anatase phase) |
| Silica-Zirconia Cogel (3% $ZrO_2$, enriched in shell of $SiO_2$) |
| Silica with monoclinic-Zirconia (10%) |
| Silica doped with Zirconia (5%) |
| monoclinic-Zirconia (95%+) |
| tetragonal-Zirconia (95%+) |
| Tungstated tetragonal-Zirconia (18% $WO_3$) |
| Carbon (93%+) |

Silicotungstic acid hydrate was dissolved in water and then a support according to Table 1 was added to this solution (which was always in excess of the pore volume and voidage of the support). The mass of each reagent is given in Table 2 below. The support was allowed to contact the solution for at least 1 hour with occasional gentle swirling to dislodge any trapped air bubbles before the excess solution was drained, under gravity, from the support. The catalyst was allowed to drain for between 15 to 60 minutes until no more liquid was removed from the support. After draining was complete, the catalyst was transferred to a ceramic tray and dried in an oven at between 110° C. and 130° C. to give the dried solid catalyst.

The dried solid catalyst was weighed and the amount of silicotungstic acid adsorbed on the catalyst calculated by difference in weight to the starting support material as indicated in Table 2.

mol/hr) and helium (0.00107 mol/hr) flow and held at this temperature for 8 hours before being cooled to 150° C.

Ethanol (0.04084 mol/hr) was then added to the nitrogen/helium flow and the temperature was increased at 2° C./min to 225° C. Once at 225° C. the feed pressure was increased at a rate of 0.1 MPa/min such that the pressure inside the reactor was increased to the value of 27.57 MPa. Once at the desired pressure diethyl ether and water were added to the ethanol, helium and nitrogen flow and the flows of the feed components adjusted to give ethanol (0.02677 mol/hr), diethyl ether (0.00776 mol/hr), water (0.00297 mol/hr), helium (0.00106 mol/hr) and nitrogen (0.01479 mol/hr).

TABLE 2

| Catalyst | Example | Support | Mass of Support (g) | STA (g) | Water (g) | Dried catalyst (g) | STA Loading (g/kg) |
| --- | --- | --- | --- | --- | --- | --- | --- |
| A | Comparative | Silica - Aerolyst 3045 | 30.01 | 14.91 | 73.28 | 34.76 | 136.6 |
| B | Comparative | Silica - Aerolyst 3045 | 512.00 | 508.00 | 1249.00 | 678.35 | 245.2 |
| C | Comparative | Silica - Aerolyst 3045 | 458.39 | 913.40 | 1123.00 | 735.30 | 376.6 |
| D | Comparative | Silica - Cariact Q15 | 430.00 | 430.00 | 976.00 | 591.37 | 272.7 |
| E | Comparative | Silica - Grace Davison G57 | 20.05 | 21.54 | 49.13 | 27.77 | 278.0 |
| F | Comparative | monoclinic-Zirconia (95%+) | 15.90 | 4.58 | 16.52 | 18.43 | 137.3 |
| G | Comparative | tetragonal-Zirconia (95%+) | 15.17 | 9.12 | 20.07 | 18.89 | 196.9 |
| H | Example | m/t-Zirconia-Titania (41% anatase phase) | 15.34 | 8.11 | 20.10 | 18.60 | 175.3 |
| I | Example | Silica with monoclinic-Zirconia (10%) | 10.02 | 5.73 | 25.10 | 12.90 | 223.3 |
| J | Example | Silica doped with Zirconia (5%) | 10.07 | 8.11 | 25.02 | 13.25 | 240.0 |
| K | Example | Silica-Zirconia Cogel (3% $ZrO_2$, enriched in shell of $SiO_2$) | 10.20 | 16.22 | 21.94 | 20.83 | 510.3 |
| L | Example | Silica-Zirconia Cogel (3% $ZrO_2$, enriched in shell of $SiO_2$) | 10.00 | 8.14 | 22.00 | 15.24 | 343.8 |
| M | Example | Tungstated tetragonal-Zirconia (18% $WO_3$) | 14.48 | 4.50 | 16.10 | 16.15 | 103.2 |
| N | Comparative | Titania (100% with 75% anatase phase) | 8.02 | 2.04 | 2.93 | 9.81 | 181.8 |
| O | Example | Silica-Titania Cogel (3% $TiO_2$, enriched in shell of $SiO_2$) | 5.02 | 3.32 | 11.50 | 7.31 | 313.3 |
| P | Example | Silica-Titania Cogel (3% $TiO_2$, enriched in shell of $SiO_2$) | 4.98 | 7.58 | 11.03 | 11.26 | 557.7 |
| Q | Example | Silica-Titania Cogel (3% $TiO_2$, dispersed homogeneously throughout $SiO_2$) | 5.06 | 5.04 | 11.66 | 7.71 | 343.5 |
| R | Example | Silica doped with Titania (5%) | 10.13 | 6.89 | 25.00 | 12.97 | 219.0 |
| S | Example | Silica-Titania (32%) | 10.03 | 9.73 | 25.11 | 13.19 | 239.6 |
| T | Comparative | Silica-Titania (51%) | 10.05 | 10.01 | 25.07 | 12.89 | 220.3 |
| U | Comparative | Silica-Titania (70%) | 10.23 | 7.64 | 25.03 | 12.37 | 173.0 |
| V | Example | Silica-Niobia (10%) | 10.10 | 5.89 | 25.28 | 13.20 | 234.8 |
| W | Comparative | Carbon (93%+) | 4.49 | 4.60 | 20.42 | 6.54 | 313.9 |
| X | Comparative | γ-Alumina | 8.08 | 1.99 | 10.00 | 9.38 | 138.9 |
| Y | Comparative | Silica-Alumina (25%) | 10.07 | 10.11 | 23.03 | 13.54 | 256.3 |
| Z | Comparative | Silica doped with Alumina (7%) | 10.02 | 6.32 | 25.11 | 12.16 | 176.0 |
| AA | Comparative | Alumino-silicate | 30.32 | 46.71 | 50.53 | 42.68 | 289.6 |
| AB | Example | Tungstated tetragonal-Zirconia (18% $WO_3$) | 30.17 | 27.55 | 32.26 | 39.43 | 234.8 |

General Procedure for Vapour Phase Dehydration of Ethanol with Supported Silicotungstic Acid A mass of supported silicotungstic acid catalyst (as indicated in Table 3 below) prepared in accordance with the above method was loaded into a reactor tube having an isothermal bed and pressurised to 0.501 MPa under inert gas (nitrogen and helium) flow. The catalyst was heated at 2° C./min to 240° C. under a combined nitrogen (0.01500

Once the catalyst performance had stabilised to a steady-state at 225° C., typically after around 100 hrs, the catalyst temperature, which is the same as the feed temperature in this particular reactor, was increased to 260° C. and the ethylene productivity monitored versus time by on-line GC analysis.

TABLE 3

| Expt. No. | Plate | Catalyst | Support | STA Loading (g/kg) | Mass of catalyst in Reactor (mg) | STA in Reactor (mg) |
|---|---|---|---|---|---|---|
| 1 | 5 | B | Silica - Aerolyst 3045 | 245.2 | 54.34 | 13.5 |
| 2 | 5 | X | γ-Alumina | 138.9 | 98.9 | 13.7 |
| 3 | 5 | F | monoclinic-Zirconia (95%+) | 137.3 | 100.09 | 13.7 |
| 4 | 5 | L | Silica-Zirconia Cogel (3% $ZrO_2$, enriched in shell of $SiO_2$) | 343.8 | 40 | 13.8 |
| 5 | 5 | W | Carbon (93%+) | 313.9 | 43.77 | 13.7 |
| 6 | 5 | Y | Silica-Alumina (25%) | 256.3 | 53.6 | 13.7 |
| 7 | 5 | Q | Silica-Titania Cogel (3% $TiO_2$, dispersed homogeneously throughout SiO2) | 343.5 | 40.01 | 13.7 |
| 8 | 5 | M | Tungstated tetragonal-Zirconia (18% $WO_3$) | 103.2 | 133.1 | 13.7 |
| 9 | 5 | O | Silica-Titania Cogel (3% $TiO_2$, enriched in shell of $SiO_2$) | 313.3 | 43.91 | 13.8 |
| 10 | 7 | AA | Alumino-silicate | 289.6 | 47.4 | 13.7 |
| 11 | 7 | B | Silica - Aerolyst 3045 | 245.2 | 54.3 | 13.5 |
| 12 | 7 | N | Titania (100% with 75% anatase phase) | 181.8 | 75.6 | 13.7 |
| 13 | 7 | F | monoclinic-Zirconia (95%+) | 137.3 | 100.1 | 13.7 |
| 14 | 7 | P | Silica-Titania Cogel (3% $TiO_2$, enriched in shell of $SiO_2$) | 557.7 | 24.6 | 13.7 |
| 15 | 7 | K | Silica-Zirconia Cogel (3% $ZrO_2$, enriched in shell of $SiO_2$) | 510.3 | 27 | 13.8 |
| 16 | 7 | J | Silica doped with Zirconia (5%) | 240.0 | 57.3 | 13.8 |
| 17 | 7 | Z | Silica doped with Alumina (7%) | 176.0 | 78.2 | 13.8 |
| 18 | 7 | V | Silica with Niobia (10%) | 234.8 | 58.5 | 13.7 |
| 19 | 7 | R | Silica doped with Titania (5%) | 219.0 | 62.7 | 13.7 |
| 20 | 7 | I | Silica with monoclinic-Zirconia (10%) | 223.3 | 61.6 | 13.8 |
| 21 | 7 | H | m/t-Zirconia-Titania (41% anatase phase) | 175.3 | 78.4 | 13.7 |
| 22 | 7 | G | tetragonal-Zirconia (95%+) | 196.9 | 69.9 | 13.8 |
| 23 | 7 | S | Silica-Titania (32%) | 239.6 | 57.4 | 13.8 |
| 24 | 7 | T | Silica-Titania (51%) | 220.3 | 62.5 | 13.8 |
| 25 | 7 | U | Silica-Titania (70%) | 173.0 | 79.5 | 13.8 |
| 26 | 5 | D | Silica - Cariact Q15 | 272.7 | 50.44 | 13.8 |
| 27 | 5 | E | Silica - Grace Davison G57 | 278.0 | 49.44 | 13.7 |
| 28 | 1 | B | Silica - Aerolyst 3045 | 245.2 | 54.3 | 13.5 |
| 29 | 1 | A | Silica - Aerolyst 3045 | 136.6 | 94.9 | 13.3 |
| 30 | 1 | C | Silica - Aerolyst 3045 | 376.6 | 49.1 | 18.5 |
| 31 | 1 | B | Silica - Aerolyst 3045 | 245.2 | 81.4 | 20.2 |
| 32 | 7 | AB | Tungstated tetragonal-Zirconia (18% $WO_3$) | 234.8 | 58.6 | 13.8 |

Example 1

Vapour phase dehydration of ethanol was conducted independently with catalysts B, F, G, H, I J, K, L, M and AB (Experiments Nos. 1, 3, 4, 8, 11, 13, 15, 16, 20, 21, 22, 32 from Table 3) according to the above procedure. These results of the reactions are illustrated graphically in FIG. 1.

The results show the benefit of using a mixed oxide support in accordance with the present invention for extending the heteropolyacid catalyst lifetime and reducing catalyst deactivation. Catalysts H, I, J, K, L and M employed in Experiments 4, 8, 15, 16, 20 and 21 according to Table 3, which includes catalysts comprising silica supports modified with zirconia (Catalysts I to L), a zirconia support modified by titania (Catalyst H) or a tungstated zirconia support (Catalyst M) in accordance with the invention, retain higher levels of ethylene productivity over the course of the reactions than Catalysts B, F and G employed in Experiments 1, 3, 11, 13 and 22, which include single oxide supports of silica or zirconia.

Moreover, it is also apparent that supported catalysts according to the present invention retain well over 25% of their maximum activity, observed for the same operating conditions, even after 200 hours of operation of the process with the same catalyst under the same conditions without regeneration.

It can also be seen that the initial ethylene productivity of a catalyst comprising a zirconia support is improved by modifying with titania, as illustrated by a comparison of the initial ethylene productivities of Catalyst H (Experiment 21) and Catalysts F and G (Experiments 3, 13 and 22).

Example 2

Vapour phase dehydration of ethanol was conducted independently with catalysts B, N, O, P, Q, R, S, T, U (Experiments Nos. 1, 7, 9, 11, 12, 14, 19, 23, 24 and 25 from Table 3) according to the above procedure. The results of the reactions are illustrated graphically in FIG. 2.

The results show the benefit of using a mixed oxide support in accordance with the present invention for extending the heteropolyacid catalyst lifetime and reducing catalyst deactivation. Catalysts O, P, Q, R and S employed in Experiments 7, 9, 14, 19 and 23 according to Table 3, which includes catalysts comprising silica supports modified with less than 50 wt. % titania (Catalysts O to S) retain higher levels of ethylene productivity over the course of the reactions than Catalysts B, N, T and U employed in Experiments 1, 11, 12, 24 and 25, which include single oxide supports of silica (Catalysts B and N) or silica-titania supports comprising less than 50 wt. % silica (Catalysts T and U).

Moreover, it is also apparent that supported catalysts according to the present invention retain well over 25% of their maximum activity, observed for the same operating conditions, even after 200 hours of operation of the process with the same catalyst under the same conditions and without regeneration.

Example 3

Vapour phase dehydration of ethanol was conducted independently with catalysts B, M, V and W (Experiments Nos. 1, 5, 8, 11 and 18 from Table 3) according to the above procedure. The results of the reactions are illustrated graphically in FIG. 3.

The results show the benefit of using a mixed oxide support in accordance with the present invention for extending the heteropolyacid catalyst lifetime and reducing catalyst deactivation. Catalysts M and V employed in Experiments 8 and 18 according to Table 3, which includes catalysts comprising a zirconia support modified with tungsten oxide (Catalyst M) or a silica support modified with niobia (Catalyst V) retain higher levels of ethylene productivity over the course of the reactions than Catalysts B and W employed in Experiments 1, 5 and 11, which include single oxide supports of silica (Catalyst B) or carbon (Catalyst W).

Moreover, it is also apparent that supported catalysts according to the present invention retain well over 25% of their maximum activity, observed for the same operating conditions, even after 200 hours of operation of the process with the same catalyst under the same conditions and without regeneration.

Example 4

Vapour phase dehydration of ethanol was conducted independently with catalysts B, X, Y, Z and AA (Experiments Nos. 1, 2, 6, 10, 11 and 17 from Table 3) according to the above procedure. The results of the reactions are illustrated graphically in FIG. 4.

The results show detrimental effects of the presence of alumina in a silica based support on heteropolyacid catalyst lifetime and catalyst deactivation. Catalyst B employed in Experiments 1 and 11 according to Table 3, which includes a silica support without any transition metal oxide, does not retain catalyst activity well and is almost completely deactivated after 250 hours of operation of the process. However, catalyst lifetime is not improved by modifying the silica support with alumina and initial catalyst productivity is instead severely reduced as shown with the results for Catalysts AA, Y and Z which have increasing content of alumina, employed in Experiments 6, 10 and 11 according to Table 3. The worst performing catalyst is that having a pure alumina support, corresponding to Catalyst X employed in Experiment 2.

Example 5

Vapour phase dehydration of ethanol was conducted independently with catalysts B, D and E (Experiments Nos. 1, 11, 26 and 27 from Table 3) according to the above procedure. The results of the reactions are illustrated graphically in FIG. 5.

The results show the similarity in the results for catalysts comprising different single oxide silica supports. All exhibit inferior heteropolyacid catalyst lifetime compared to mixed oxide supported heteropolyacids used in accordance with the present invention and are completely deactivated after 250 hours of operation of the process without regeneration.

Example 6

Vapour phase dehydration of ethanol was conducted independently with catalysts A and B (Experiments Nos. 28 and 29 from Table 3) according to the above procedure. The results of the reactions are illustrated graphically in FIG. 6.

The results show the similarity in the results for catalysts comprising single oxide silica supports with different loadings of silicotungstic acid (136.6 g/kg and 245.2 g/kg for Catalysts A and B respectively). Catalyst deactivation, as illustrated by a reduction in ethylene productivity (which is based on the number of moles/g of silicotungstic acid) in these reactions, is not dependent on the loading of the catalyst on the support.

Example 7

Vapour phase dehydration of ethanol was conducted independently with catalysts B and C (Experiments Nos. 30 and 31 from Table 3) according to the above procedure. The results of the reactions are illustrated graphically in FIG. 7.

The results show the similarity in the results for catalysts comprising single oxide silica supports with different loadings of silicotungstic acid (245.2 g/kg and 376.6 g/kg for Catalysts B and C respectively). Catalyst deactivation, as illustrated by a reduction in ethylene productivity (which is based on the number of moles/g of silicotungstic acid) in these reactions, is not dependent on the loading of the catalyst on the support.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope and spirit of this invention.

The invention claimed is:

1. A process for vapour phase chemical dehydration of ethanol in a reactor in the presence of a supported heteropolyacid catalyst comprising a support, wherein the support of the supported heteropolyacid catalyst is selected from: i) a first mixed oxide support comprising silica and a transition metal oxide selected from an oxide of Nb or W, wherein silica is present in an amount of at least 50 wt. %, based on the weight of the mixed oxide support; or ii) a second mixed oxide support comprising zirconia and a transition metal oxide selected from an oxide of W, Ti, Nb, Y or La, wherein zirconia is present in an amount of at least 50 wt %, based on the weight of the mixed oxide support; said process comprises the steps of: a) contacting ethanol with the supported heteropolyacid catalyst and attaining steady-state performance of the catalyst; and b) operating continuously with the supported heteropolyacid catalyst for at least 150 hours, without any regeneration of the supported heteropolyacid catalyst.

2. The process according to claim 1, wherein, operating continuously in step b) with the supported heteropolyacid catalyst is for at least 200 hours without any regeneration of the supported heteropolyacid catalyst.

3. The process according to claim 1, wherein the supported heteropolyacid catalyst retains at least 25 of its maximum activity, observed for an operating temperature under steady-state conditions, after at least 200 hours of operation of the process.

4. The process according to claim 1, wherein the support of the supported heteropolyacid catalyst is the first mixed oxide support.

5. The process according to claim 1, wherein the support of the supported heteropolyacid catalyst is the second mixed oxide support.

6. The process according to claim 5, wherein the different transition metal oxide of the second mixed oxide support is an oxide of Ti or Nb.

7. The process according to claim 1, wherein the transition metal oxide is present in the first or second mixed oxide support in an amount from 1 to 40 wt. %.

8. The process according to claim 1, wherein the heteropolyacid catalyst is a phosphotungstic or a silicotungstic acid.

9. The process according to claim 1, wherein a feed temperature of a feed-stream comprising the ethanol is from 180° C. to 270° C.

10. The process according to claim 1, wherein the process is operated at an internal reactor pressure of from 0.1 MPa to 4.5 MPa.

11. The process according to claim 1, wherein the supported heteropolyacid catalyst retains at least 85% of its maximum activity, observed for an operating temperature under steady-state conditions, after at least 200 hours of operation of the process.

12. The process according to claim 1, wherein the first mixed oxide support comprises at least 60 wt. % silica.

13. The process according to claim 1, wherein the second mixed oxide support comprises at least 60 wt. % zirconia.

14. A method of increasing catalyst lifetime in a monohydric alcohol dehydration process, said method comprising supplying a supported heteropolyacid catalyst comprising a support to the monohydric alcohol dehydration process, wherein the supported heteropolyacid catalyst comprises: i) a first mixed oxide support comprising silica and a transition metal oxide selected from an oxide of Nb or W, wherein silica is present in an amount of at least 50 wt. %, based on the weight of the mixed oxide support; or ii) a second mixed oxide support comprising zirconia and a transition metal oxide selected from an oxide of W, Ti, Nb, Y or La, wherein zirconia is present in an amount of at least 50 wt, based on the weight of the mixed oxide support.

15. The method according to claim 14, wherein the transition metal oxide of the second mixed oxide support is an oxide of Ti or M.

16. The method according to claim 14, wherein the monohydric alcohol dehydration process is an ethanol dehydration process.

* * * * *